(12) United States Patent
Ptchelintsev et al.

(10) Patent No.: US 6,562,321 B2
(45) Date of Patent: May 13, 2003

(54) COMPOSITIONS AND METHODS FOR TREATING HYPERPIGMENTATION

(75) Inventors: Dmitri Ptchelintsev, Jersey City, NJ (US); Christos D. Kyrou, Suffern, NY (US); Harish Mahalingam, Westwood, NJ (US)

(73) Assignee: Avon Products, Inc., New York, NY (US)

( * ) Notice: Subject to any disclaimer, the term of this patent is extended or adjusted under 35 U.S.C. 154(b) by 0 days.

(21) Appl. No.: 09/741,383

(22) Filed: Dec. 20, 2000

(65) Prior Publication Data

US 2002/0141953 A1 Oct. 3, 2002

(51) Int. Cl.⁷ ................................................ A61K 7/135
(52) U.S. Cl. ........................ 424/62; 424/401; 424/725; 424/757; 424/776
(58) Field of Search ................ 424/401, 725, 424/757, 776, 62

(56) References Cited

U.S. PATENT DOCUMENTS

| | | | |
|---|---|---|---|
| 6,004,543 A | | 12/1999 | Galey .......................... 424/62 |
| 6,080,393 A | * | 6/2000 | Liu et al. ................. 424/78.03 |
| 6,087,385 A | * | 7/2000 | Pershadsingh et al. ...... 514/376 |
| 6,284,234 B1 | * | 9/2001 | Niemiec et al. .......... 424/78.07 |
| 6,313,085 B1 | * | 11/2001 | Le Hen-Ferrenbach ..... 510/428 |

FOREIGN PATENT DOCUMENTS

| | | |
|---|---|---|
| BE | 1000724 | 3/1989 |
| CA | 2256085 | 7/1999 |
| EP | 968 707 | 6/1999 |
| EP | 962 224 | 12/1999 |
| RO | 111016 | 6/1996 |
| WO | WO 90/06104 | 6/1990 |
| WO | WO 99/67230 | 12/1999 |

* cited by examiner

*Primary Examiner*—Thurman K. Page
*Assistant Examiner*—Liliana Di Nola-Baron
(74) *Attorney, Agent, or Firm*—Ohlandt, Greeley, Ruggiero & Perle, L.L.P.

(57) ABSTRACT

There is provided a topical composition for treating, preventing or ameliorating hyperpigmentation in human skin. The composition has a de-pigmenting agent in an amount effect to reduce or diminish pigmentation at an area of skin to which it is applied, and a cosmetically or pharmaceutically acceptable vehicle. Suitable de-pigmenting agents include 3,3'-thiodipropionic acid, thiazolidine-2-carboxylic acid, kaempferol-7-glucoside, perilla oil, and clofibrate and clofibrate analogs and derivatives. There is also provided methods for treating, preventing or ameliorating hyperpigmentation in human skin.

26 Claims, No Drawings

COMPOSITIONS AND METHODS FOR TREATING HYPERPIGMENTATION

BACKGROUND OF THE INVENTION

1. Field of the Invention

The present invention relates to compositions useful in treating hyperpigmentation of human skin. Further, the present invention relates to methods of applying the compositions to the skin to effect treatment.

2. Description of the Prior Art

Human skin color is determined primarily by the content of the pigment melanin in the basal epidermis layer. Melanin is synthesized by the process of melanogenesis within melanocytes (pigment-producing cells). Melanin is deposited onto melanosomes, which are transferred to keratinocytes in the basal epidermal layer. Melanosomes present in these basal keratinocytes are the key determinants of skin color. The keratinocytes leave the basal layer and undergo differentiation forming the cornified top layer of the skin. Once the keratinocytes leave the basal layer, the melanosomes lose their characteristic electron dense structure, and the load of melanin is carried to the surface of the skin by the differentiating keratinocytes.

The skin can become hyperpigmented when too much melanin concentrates at one area or portion of the skin due to the retention time of the melanosomes in the basal layer. Hyperpigmentation can also occur as a result of overexposure to the sun or other inflammatory stimuli. Hyperpigmentation can take the form of solar lentigines (age spots), ephilides (freckles), melasma, chloasma, and pigmented keratoses.

The prior art discloses ways to treat hyperpigmentation by application of skin lightening agents. Representative skin lightening agents include hydroquinone and Vitamin C. Such agents typically lighten the skin by inhibiting the expression of tyrosinase enzymes involved in melanogenesis.

It would be desirable to have a way to treat hyperpigmentation by application of agents that reduce the ability of epidermal cells to retain melanin. A reduction in ability to retain melanin would speed the transfer of the melasonomes to the keratinocytes and allow existing hyperpigmented portions of the skin to be lightened or de-pigmented faster than with conventional skin lightening agents, which act primarily to inhibit the formation of new melanin.

SUMMARY OF THE INVENTION

It is an object of the present invention to provide a composition and method for treating, preventing and/or ameliorating hyperpigmentation of human skin.

It is still another object of the present invention to provide such a composition and method that has one or more agents that decrease the retention time of melanosomes at the basal layer. This is achieved by inhibiting the ability of epidermal cells to retain or uptake melanin/melanosomes and/or increase the rate of transport of basal keratinocytes to the surface of the skin.

These and other objects of the present invention are achieved by a method and composition that comprises (a) a de-pigmenting agent in an amount effective to prevent, treat and/or ameliorate pigmentation at an area of skin to which it is applied, and (b) a cosmetically or pharmaceutically acceptable vehicle. Suitable de-pigmenting agents include 3,3'-thiodipropionic acid, thiazolidine-2-carboxylic acid, Kaempferol-7-glucoside, perilla oil, and clofibrate and clofibrate analogs and/or derivatives, as well as those set forth below.

DETAILED DESCRIPTION OF THE INVENTION

The present invention provides for de-pigmenting compositions containing an effective amount of one or more depigmenting agents which, when applied to human skin, prevent, treat and/or ameliorate pigmentation at the area or portion of skin to which they are applied. The compositions are effective at reducing or diminishing pigmented areas or portions of the skin such as age spots, freckles, melasma, chloasma, and pigmented keratoses. The compositions are topically applied to the skin.

A first embodiment of the present composition has a de-pigmenting agent corresponding to the following formula (I):

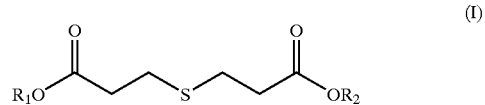

wherein $R_1$ and $R_2$ are independently selected from the group of substituents consisting of hydrogen; alkyls, substituted or unsubstituted, branched or linear; alkenyls, substituted or unsubstituted, branched or linear, and having up to 5 double bonds; alkynyls, substituted or unsubstituted, branched or linear and having up to 5 triple bonds; aryls, substituted or unsubstituted; cycloalkyls, substituted and unsubstituted; and cycloalkenyls, substituted and unsubstituted.

Preferably, the de-pigmenting agent of Formula I is 3,3'-thiodipropionic acid, wherein $R_1$ and $R_2$ are hydrogen.

A second embodiment of the present composition has a de-pigmenting agent corresponding to the following formula (II):

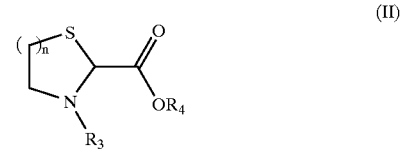

wherein $R_3$ and $R_4$ are defined the same as $R_1$ and $R_2$ in formula (I) above; in addition, $R_3$ can be an acyl group; wherein "n" is an integer from 1 to 4, preferably 1 to 3, and most preferably 1 to 2.

Preferably, the de-pigmenting composition of Formula II is thiazolidine-2-carboxylic acid, wherein $R_3$ and $R_4$ are hydrogen and n=1.

In a third embodiment of the present composition, the de-pigmenting agent is perilla oil. Perilla oil is derived from the seeds of the mint of the genus Perilla.

In a fourth embodiment of the present composition, the de-pigmenting agent is clofibrate or a clofibrate analog or derivative. Clofibrate is ethyl 2-(p-chlorophenoxy) isobutyrate, which corresponds to the following formula (IV):

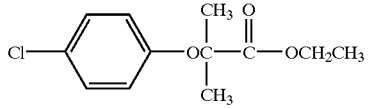

A fifth embodiment of the present composition has a de-pigmenting agent corresponding to the following formula (III):

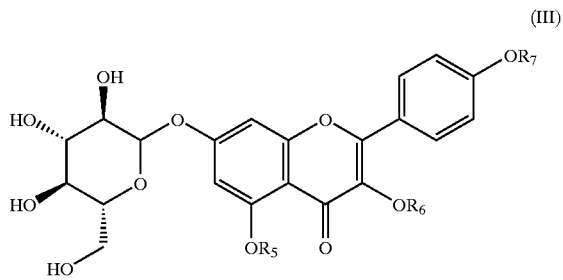

wherein $R_5$, $R_6$, and $R_7$ are as defined as for $R_1$ and $R_2$ in formula (I) above.

Preferably, the de-pigmenting agent of Formula III is kaempferol-7-glycoside wherein $R_5$, $R_6$ and $R_7$ are hydrogen. Kaempferol-7-glycoside is believed to reduce pigmentation by inhibiting tyrosinase but may also reduce pigmentation by alternate pathways.

In a sixth embodiment of the present invention, the de-pigmenting agent is a combination of one or more of the above de-pigmenting agents. Preferably, the combination includes de-pigmenting agents that utilize different mechanisms of action. A preferred combination includes kaempferol-7-glucoside and perilla oil or clofibrate (or a clofibrate analog or derivative).

The de-pigmenting agent is present in the composition at an amount effect to prevent, treat, or ameliorate pigmentation at the area or portion of skin to which it is applied. The de-pigmenting agent is preferably present at about 0.0001 percentage by weight (wt %) to about 98 wt %, more preferably at about 0.001 wt % to about 30 wt %, and most preferably at about 0.05 wt % to about 10 wt % based on the total weight of the composition.

The composition comprises a pharmaceutically and/or cosmetically acceptable vehicle to provide bulk and physical form. Preferably, the vehicle is hypoallergenic, as allergens and other irritating agents exacerbate pigmentation. Suitable vehicles include, but are not limited to, cetyl alcohol, ethanol, glycerin, myristyl palmitate, polyvinyl alcohol, propylene glycol, propanol, and water, and mixtures thereof. The de-pigmenting agent is admixed with the vehicle(s) along with any other adjuvants or ingredients to form the topical composition. The de-pigmenting agent can also be incorporated into liposomes.

The present composition may take any suitable form such as a solution, cream, serum, stick, patch, mask, towelette, lotion, emulsion, ointment or gel.

The present composition may optionally have one or more of the following ingredients: anesthetics, antiallergenics, antimicrobial agents, antiseptics, chelating agents, colorants, demulcents, emollients, emulsifiers, exfoliants, fragrances, humectants, lubricants, moisturizers, preservatives, skin penetration enhancers, stabilizers, surfactants, thickeners, viscosity modifiers, vitamins, and mixtures thereof.

The present invention may also include conventional hypopigmenting agents, such as hydroquinone, ascorbic acid (Vitamin C) and/or licorice extract; retinoids, such as retinol or retinoic acid; anti-inflammatory agents, such as bisabolol, anti-acne agents, such as salicylic acid; exfoliants, such as alpha-hydroxy acids, beta-hydroxy acids, keto acids, oxa acids or oxa diacids (disclosed in U.S. Pat. Nos. 5,847,003 and 5,834,513); ascorbyl-phosphoryl-cholesterol (disclosed in U.S. Pat. No. 5,866,147); sunscreens, such as oxybenzone, octyl methoxycinnamate, octyl salicylate, octocrylene, titanium dioxide, zinc oxide, butyl methoxydibenzoylmethane, methylene bis-benzotriazoylteramehtylbuthylphenol (MBBT), bis-ethylhexyl oxyphenol methoxyphenol triazine (BEMT); or any combination thereof. When conventional hypopigmenting agents are included in a composition of the present invention, it is preferred that the hypopigmenting agent has a mechanism of action that complements the mechanism of action of the depigmenting agent of the present invention. Preferred alpha-hydroxy acids include lactic acid, glycolic acid, or a mixture thereof. The preferred oxa diacid is 3,6,9-trioxaundecanedioic acid.

EXAMPLE

| Ingredient | wt % |
|---|---|
| De-pigmenting agent | 0.001 to 98 |
| pH adjusting agent (e.g. ammonium hydroxide | 0.001 to 4 |
| Humectants (e.g. glycols, glycerols) | 0.5 to 15 |
| Thickeners (e.g. gums, starches polymers) | 0.1 to 4 |
| Chelating Agents (e.g. EDTA) | 0.001 to 0.5 |
| Emollients (e.g. isopropyl myristate, fatty esters) | 1 to 10 |
| Silicones (cyclomethicone-pentamer) | 0.1 to 15 |
| Preservative (e.g. parabens) | 0.01 to 2 |
| Alcohols (e.g. ethanol) | 0 to 10 |
| Antioxidants (e.g. vitamin E acetate) | 0.01 to 5 |
| Anti-inflammatory (e.g. bisabolol) | 0.01 to 10 |
| Sunscreen (e.g. titanium dioxide, benzophenone-3, butyl methoxydibenzoylmethane) | 0.01 to 15 |
| Water | q.s. |

The present invention having been described with particular reference to the preferred forms thereof, it will be obvious that various changes and modifications may be made herein without departing from the spirit and scope of the invention as defined in the appended claims. As used herein, singular can mean plural.

What is claimed is:

1. A topical composition, comprising:

a) a de-pigmenting agent selected from the group consisting of:

(i)

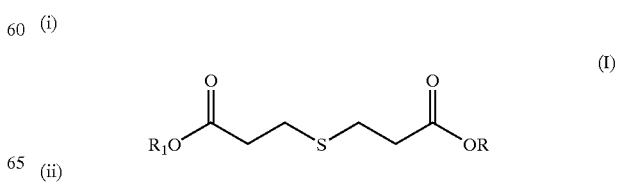

(ii)

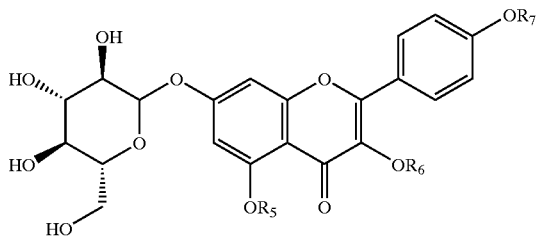

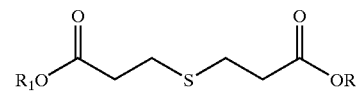

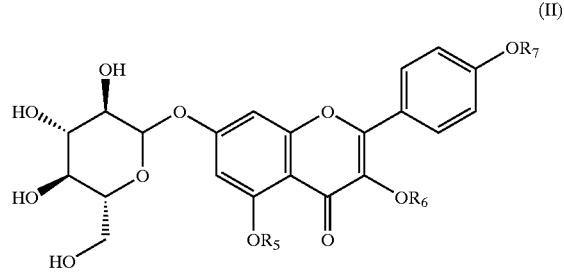

(iii) perilla oil;
(iv) clofibrate and
(v) any combination thereof; and b) a vehicle, wherein the de-pigmenting agent is present in an amount effective to prevent, ameliorate or treat the hyperpigmentation of the skin, and wherein $R_1$, $R_2$, $R_5$, $R_6$ and $R_7$ are independently selected from the group of substituents consisting of hydrogen; alkyls, substituted or unsubstituted, branched or linear; alkenyls, substituted or unsubstituted branched or linear, and having up to 5 double bonds; alkynyls, substituted or unsubstituted branched or linear and having up to 5 triple bonds; aryls, substituted or unsubstituted; cycloalkyls; and cycloalkenyls.

2. The composition of claim 1, wherein the de-pigmenting agent is present from about 0.0001 wt % to about 98 wt % based on the total weight of the composition.

3. The composition of claim 1, wherein the de-pigmenting agent is present from about 0.001 wt % to about 30 wt % based on the total weight of the composition.

4. The composition of claim 1, wherein the de-pigmenting agent corresponds to formula (I).

5. The composition of claim 4, wherein the de-pigmenting agent is 3,3'-thiodipropionic acid.

6. The composition of claim 1, wherein the de-pigmenting agent corresponds to formula (II).

7. The composition of claim 6, wherein the de-pigmenting agent is kaempferol-7-glucoside.

8. The composition of claim 1, wherein the de-pigmenting agent is perilla oil.

9. The composition of claim 1, wherein the de-pigmenting agent is clofibrate.

10. The composition of claim 1, wherein the de-pigmenting agent is a combination selected from the group consisting of:
    (a) perilla oil and kaempferol-7-glucoside; and
    (b) clofibrate and kaempferol-7-glucoside.

11. The composition of claim 1, further comprising an ingredient selected from the group consisting of hydroquinone, ascorbic acid, licorice extract, retinoid, bisabolol, salicylic acid, an oxa acid, oxa diacid, an alpha hydroxy acid, a beta hydroxy acid, a keto acid, and any combination thereof.

12. The composition of claim 11, wherein the ingredient is selected from the group consisting of: lactic acid, glycolic acid, 3,6,9-trioxaundecanedioic acid, and any combination thereof.

13. A method of preventing, ameliorating, or treating hyperpigmentation of skin comprising topically applying to the skin a composition comprising:
    a) a de-pigmenting agent selected from the group consisting of:

(i)

(ii)

(iii) perilla oil;
(iv) clofibrate and
(v) any combination thereof; and b) a vehicle, wherein the de-pigmenting agent is present in an amount effective to prevent, ameliorate or treat the hyperpigmentation of the skin, and wherein $R_1$, $R_2$, $R_5$, $R_6$ and $R_7$ are independently selected from the group of substituents consisting of hydrogen; alkyls, substituted or unsubstituted, branched or linear; alkenyls, substituted or unsubstituted, branched or linear, and having up to 5 double bonds; alkynyls, substituted or unsubstituted, branched or linear and having up to 5 triple bonds; aryls, substituted or unsubstituted; cycloalkyls; and cycloalkenyls.

14. The method of claim 13, wherein the de-pigmenting agent is present from about 0.0001 wt % to about 98 wt % based on the total weight of the composition.

15. The method of claim 13, wherein the de-pigmenting agent is present from about 0.001 wt % to about 30 wt % based on the total weight of the composition.

16. The method of claim 13, wherein the depigmenting agent is selected from the group consisting of:
    (a) 3,3'-thiodipropionic acid;
    (b) kaempferol-7-glucoside;
    (c) perilla oil;
    (d) clofibrate
    (e) any combination thereof.

17. The method of claim 16, wherein the de-pigmenting agent is a combination selected from the group consisting of:
    (a) perilla oil and kaempferol-7-glucoside; and
    (b) clofibrate kaempferol-7-glucoside.

18. The method of claim 16, wherein the depigmenting agent is selected from the group consisting of perilla oil, clofibrate and any combination thereof.

19. The method of claim 13, wherein the de-pigmenting agent corresponds to formula (I).

20. The method of claim 19, wherein the de-pigmenting agent is 3,3'-thiodipropionic acid.

21. The method of claim 13, wherein the de-pigmenting agent corresponds to formula (II).

22. The method of claim 21, wherein the de-pigmenting agent is kaempferol-7-glucoside.

23. The method of claim 13, wherein the de-pigmenting agent is perilia oil.

24. The method of claim 23, wherein the de-pigmenting agent is clofibrate.

25. The method of claim 13, the composition further comprises an ingredient selected from the group consisting of hydroguinone, ascorbic acid, licorice extract, retinoid, bisabolol, salicylic acid, an oxa acid, oxa diacid, an alpha hydroxy acid, a beta hydroxy acid, a keto acid, and any combination thereof.

26. The method of claim 25, wherein the ingredient is selected from the group consisting of: lactic acid, glycolic acid, 3,6,9-trioxaundecanedioic acid, and any combination thereof.

* * * * *